United States Patent [19]

Mohrbacher et al.

[11] 4,132,720
[45] Jan. 2, 1979

[54] ALKENYLGLYCIDIC ACID DERIVATIVES

[75] Inventors: Richard J. Mohrbacher, Maple Glen; Winston Ho, Hatfield; Gene F. Tutwiler, Churchville, all of Pa.

[73] Assignee: McNeil Laboratories, Inc., Fort Washington, Pa.

[21] Appl. No.: 897,972

[22] Filed: Apr. 20, 1978

[51] Int. Cl.$^2$ ............................................. C07D 303/42
[52] U.S. Cl. ............................ 260/348.61; 260/405.5; 424/278
[58] Field of Search ..................................... 260/348.61

[56] References Cited

PUBLICATIONS

Chemical Abstracts, vol. 50 (1956) 2533i.

Primary Examiner—Norma S. Milestone
Attorney, Agent, or Firm—Salvatore R. Conte

[57] ABSTRACT

Glycidic acid derivatives substituted in the 2-position with a long chain alkenyl of from 11 to 16 carbons having hypoglycemic activity.

4 Claims, No Drawings

ALKENYLGLYCIDIC ACID DERIVATIVES

DESCRIPTION OF THE INVENTION

The invention relates to novel alkenylglycidic acid derivatives having the formula:

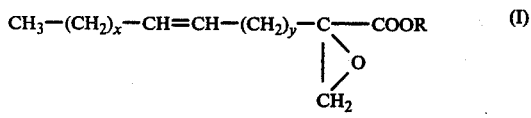

wherein x and y are each a positive integer the sum of which (x+y) equals an integer from 8 to 13, and R is a member selected from the group consisting of hydrogen and loweralkyl, preferably methyl.

As used herein, the term "loweralkyl" may be straight or branch chained saturated hydrocarbons having from 1 to about 5 carbons, e.g., methyl, ethyl, propyl, isopropyl, butyl, sec-butyl, tert-butyl, pentyl and the like.

The compounds of formula (I) may be prepared by the following synthetic procedure. An olefinic acid of formula (II), wherein x and y are as previously defined, is transformed by known formylation procedures into an α-hydroxymethylolefinic acid of formula (III). Formylation of (II) is advantageously accomplished in the presence of an equivalent amount of lithium diisopropylamide (LDA) which may be prepared in situ by the interaction of equimolar amounts of a loweralkyllithium, for example, methyllithium, n-butyllithium and the like, and diisopropylamine in an appropriate anhydrous aprotic organic solvent, for example, an ether such as dioxane, tetrahydrofuran (THF) and the like, and hexamethylphosphoramide (HMPA), etc. The interaction of the loweralkyllithium with diisopropylamine is preferably conducted in the cold (from about −40° to about 0° C.) under an inert atmosphere such as nitrogen, argon and the like.

While maintaining the solution of lithium diisopropylamide in the cold, a solution of the olefinic acid of formula (II) in an anhydrous aprotic organic solvent as indicated previously is slowly added, preferably dropwise. After addition of (II), the temperature of the mixture may be increased, for example, to about 25°–50° C. Formaldehyde is then introduced into the reaction mixture, for example, by passing formaldehyde vapors (obtained, for example, by thermal depolymerization of paraformaldehyde) in a stream of inert gas over the surface of the mixture or by bubbling formaldehyde through the mixture. The former is preferred for technical advantages since bubbling often causes clogging of the feed apparatus due to repolymerization of the formaldehyde. The formaldehyde may also be introduced into the reaction vessel as a pre-prepared at about −78° C. formaldehyde-tetrahydrofuran solution. Such formaldehyde-tetrahydrofuran solution may be prepared by cooling the formaldehyde vapor in a vessel containing anhydrous tetrahydrofuran. After the formylation reaction is complete, the reaction mixture is cooled, preferably to about 0° C., and then treated with a strong mineral acid, for example, sulfuric acid, hydrochloric acid and the like to acidic pH. The formylated product (III) is then recovered from the separated organic layer by conventional techniques, e.g., evaporation of solvent, recrystallization, etc.

The thus-obtained α-hydroxymethylolefinic acid of formula (III) is then dehydrated by treatment with an appropriate dehydrating agent such as, for example, concentrated phosphoric acid, sulfuric acid and the like. and heated to distillation temperatures, thereby removing a molecule of water from (III) to form the corresponding acrylic acid derivative of formula (IV).

Bromination of (IV), for example, by treatment with an equivalent amount of liquid bromine in an inert organic solvent such as a halogenated hydrocarbon, an aromatic hydrocarbon, an ether and the like, in the cold results in bromination across the double bond of the long alkyl chain to yield the dibromoacrylic acid derivative of formula (V).

Subsequent esterification of (V) by standard techniques with an appropriate lower alcohol, for example, ethanol, propanol, isobutanol and the like affords the corresponding loweralkyl esters of formula (VI). Methyl esters may be conveniently obtained by methylation of (V) using a boron trifluoride/methanol solution under reflux conditions. The reaction mixture is then concentrated to about half its original volume, treated with suitable base, e.g., sodium or potassium bicarbonate, to about pH 7 and the resultant methyl ester (VI) extracted by conventional techniques.

Transformation of the brominated acrylate of formula (VI) to the brominated glycidates of formula (VII) is readily accomplished by treatment with an appropriate organic peracid, for example, m-chloroperbenzoic acid, trifluoroperacetic acid, peracetic acid, perphthalic acid and the like in an inert aprotic organic solvent, for example, an aromatic hydrocarbon, a halogenated hydrocarbon and the like, under reflux conditions. In order to inhibit decomposition of the peracid under such conditions, a small amount of an appropriate free radical inhibitor such as, for example, 3-tert-butyl-4-hydroxy-5-methylphenyl sulfide, may be advantageously employed. The thus-formed loweralkyl dibromoglycidate (VII) may then be isolated from the reaction mixture by standard recovery and purification techniques.

Debromination of (VII) affords the desired alkylenic glycidic acid esters of formula (I). The elimination of bromine with formation of the alkene linkage is readily accomplished by treating (VII) with zinc and anhydrous potassium carbonate in an aprotic organic solvent such as dimethylformamide (DMF), dioxane and the like. Small additions of iodine and elevated temperatures may be employed to enhance the rate of reaction. Analysis of the alkylenic product (I) so obtained, for example, by standard NMR techniques, reveals it to have the cis-configuration.

Conventional hydrolysis of the alkylenic glycidic acid esters of formula (I) is then utilized to yield the corresponding alkylenic glycidic acids of formula (I). Preferably, typical alkaline ester-to-acid hydrolysis conditions are employed, for example, by utilizing a suitable alkali metal or alkaline earth metal hydroxide to yield the corresponding acid salt followed by treatment of said salt with an appropriate mineral acid such as, for example, hydrochloric acid, sulfuric acid and the like. In turn, the acids of formula (I) may readily be re-esterified by conventional treatment with appropriate lower alkanols to yield the desired esters of formula (I).

The foregoing synthetic sequences may be illustrated by the following schematic diagram:

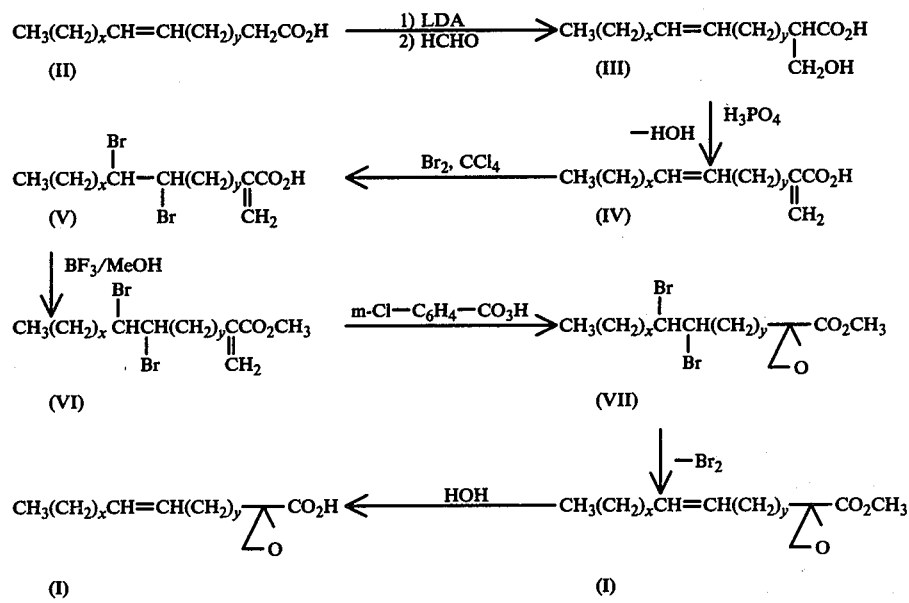

Typical loweralkyl alkenylglycidates (I) that are obtainable according to the foregoing synthetic sequence by starting with an appropriate olefinic acid of formula (II) are the following:

| Product (I) | Olefinic Acid (II) |
| --- | --- |
| methyl 2-(2,3-undecenyl)-glycidate | 4-tridecenoic acid |
| ethyl 2-(4,5-undecenyl)-glycidate | 6-tridecenoic acid |
| butyl 2-(7,8-undecenyl)-glycidate | 9-tridecenoic acid |
| pentyl 2-(3,4-dodecenyl)-glycidate | 5-tetradecenoic acid |
| methyl 2-(5,6-dodecenyl)-glycidate | 7-tetradecenoic acid |
| ethyl 2-(6,7-dodecenyl)-glycidate | 8-tetradecenoic acid |
| butyl 2-(7,8-dodecenyl)-glycidate | 9-tetradecenoic acid |
| methyl 2-(5,6-tridecenyl)-glycidate | 7-pentadecenoic acid |
| ethyl 2-(6,7-tridecenyl)-glycidate | 8-pentadecenoic acid |
| methyl 2-(7,8-tridecenyl)-glycidate | 9-pentadecenoic acid |
| methyl 2-(2,3-tetradecenyl)-glycidate | 4-hexadecenoic acid |
| ethyl 2-(4,5-tetradecenyl)-glycidate | 6-hexadecenoic acid |
| isopropyl 2-(5,6-tetradecenyl)-glycidate | 7-hexadecenoic acid |
| methyl 2-(7,8-tetradecenyl)-glycidate | 9-hexadecenoic acid |
| methyl 2-(6,7-pentadecenyl)-glycidate | 8-heptadecenoic acid |
| ethyl 2-(7,8-pentadecenyl)-glycidate | 9-heptadecenoic acid |
| butyl 2-(8,9-pentadecenyl)-glycidate | 10-heptadecenoic acid |
| methyl 2-(2,3-hexadecenyl)-glycidate | 4-octadecenoic acid |
| ethyl 2-(3,4-hexadecenyl)-glycidate | 5-octadecenoic acid |
| methyl 2-(6,7-hexadecenyl)-glycidate | 8-octadecenoic acid |
| methyl 2-(8,9-hexadecenyl)-glycidate | 10-octadecenoic acid |

Hydrolysis of the foregoing esters, as described previously, affords the corresponding acids of formula (I).

The compounds of formula (I) are useful for their hypoglycemic activity as demonstrated in a standard blood glucose tolerance test (GTT) in rats. Three to five glucose primed, fasted (18-24 hrs.), intact male rats are used for each test and control group. The compound to be tested is suspended in 0.5% aqueous methylcellulose and administered at doses of 10-150 mg/kg either intraperitoneally, subcutaneously or orally 30-60 minutes prior to administration of glucose. The glucose is given either orally (1 g/kg) or subcutaneously (0.8 g/kg). Serial blood samples are obtained from the tail without anesthesia at thirty minute intervals for 3 hours after administration of the glucose. Blood specimens are immediately deproteinized with barium hydroxide and zinc sulfate according to conventional GTT procedures and glocose levels are determined using the standard glucose oxidase assay. A significant depression of blood sugar from that of controls is observed with the subject compounds.

The following examples are intended to illustrate, but not to limit, the scope of the present invention.

EXAMPLE I

α-Hydroxymethyloleic Acid: Anhydrous tetrahydrofuran (600 ml) and 24.5 g (0.24 mole) of diisopropylamine is added to a dry three neck flask purged with nitrogen and maintained under a nitrogen atmosphere. After cooling the mixture to −20° C., 94 ml of n-butyllithium in hexane (2.6 M) (0.24 mole) is added at such a rate as to prevent the temperature from exceeding 0° C. and then 40 ml of anhydrous hexamethylphosphoramide (HMPA) (0.22 mole) is added. To the thus prepared in situ solution of lithium diisopropylamide (LDA), a solution of 28.2 g of oleic acid (0.1 mole) in 30 ml of tetrahydrofuran (THF) is added dropwise with stirring while maintaining the reaction temperature below 0° C. A milky white suspension results after the addition of oleic acid. The reaction mixture is brought to about 40° C. by using a warm water bath. The suspension changes to a clear solution as the temperature gradually reaches 40° C. This system is then connected to a formaldehyde generating system. Paraformaldehyde (20 g) is heated in a three neck flask at 180°-200° C. to generate formaldehyde and the formaldehyde vapors are carried by a stream of nitrogen over the surface of the stirred solution of α-lithiated lithium oleate prepared previously. After complete depolymerization of paraformaldehyde, the reaction solution is cooled in an ice bath and neutralized with hydrochloric acid until acidic. The organic layer is separated and is concentrated under reduced pressure on a rotary evaporator to remove most of the THF solvent. The resulting oily residue is dissolved in about 500 ml of ether, washed with 10% hydrochloric acid solution and then with water. The ether layer is dried over $Na_2SO_4$ and the solvent is removed under reduced pressure to give 23.0 g of crude product, (80% yield), α-hydroxymethyloleic acid, which is used without purification in the next synthetic step.

EXAMPLE II

By repeating the procedure of Example (I) except that an equivalent amount of each of the olefinic acids of formula (II) indicated below is substituted for the oleic acid used therein, the following α-hydroxymethyl olefinic acids are obtained as respective products:

| Olefinic acid (II) | Product |
|---|---|
| 4-tridecenoic acid | α-hydroxymethyl-4-tridecenoic acid |
| 5-tetradecenoic acid | α-hydroxymethyl-5-tetradecenoic acid |
| 9-pentadecenoic acid | α-hydroxymethyl-9-pentadecenoic acid |
| 4-hexadecenoic acid | α-hydroxymethyl-4-hexadecenoic acid |
| 9-heptadecenoic acid | α-hydroxymethyl-9-heptadecenoic acid |
| 8-octadecenoic acid | α-hydroxymethyl-8-octadecenoic acid |

EXAMPLE III 2-(cis-7,8-Hexadecenyl)-acrylic acid: A 9.0 g sample of α-hydroxymethyloleic acid (0.028 mole) and 4 drops of phosphoric acid (85%) are placed in a distillation flask and the mixture is heated to 270°–280° C. in an oil bath under vacuum. The product, 2-(cis-7,8-hexadecenyl)-acrylic acid is distilled over at 190°–195° C. at 0.05 mm Hg (4.2 g; 53% yield).

EXAMPLE IV

The dehydration procedure of Example III is repeated with an equivalent amount of each α-hydroxymethyl olefinic acid obtained in Example IV as the starting material to yield the corresponding acrylic acid products respectively:
2-(cis-2,3-undecenyl)-acrylic acid;
2-(cis-3,4-dodecenyl)-acrylic acid;
2-(cis-7,8-tridecenyl)-acrylic acid;
2-(cis-2,3-tetradecenyl)-acrylic acid;
2-(cis-7,8-pentadecenyl)-acrylic acid; and
2-(cis-6,7-hexadecenyl)-acrylic acid.

EXAMPLE V 2-(7,8-Dibromohexadecyl)-acrylic acid: To a solution of 3.5 g (0.0119 mole) of 2-(cis-7,8-hexadecenyl)-acrylic acid in 100 ml of carbon tetrachloride at 0° C. (ice water bath) is added slowly 1.90 g of liquid bromine (0.0119 mole). The solvent is removed under reduced pressure, the residue is taken up in ether, washed with water and dried over $Na_2SO_4$. Removal of the ether solvent gives 5.1 g of crude oily product, 2-(7,8-dibromohexadecyl)-acrylic acid.

EXAMPLE VI

The bromination procedure of Example V is conducted on an equivalent amount of each acrylic acid obtained in Example IV to yield the respective brominated products:
2-(2,3-dibromoundecyl)-acrylic acid;
2-(3,4-dibromododecyl)-acrylic acid;
2-(7,8-dibromotridecyl)-acrylic acid;
2-(2,3-dibromotetradecyl)-acrylic acid;
2-(7,8-dibromopentadecyl)-acrylic acid; and
2-(6,7-dibromohexadecyl)-acrylic acid.

EXAMPLE VII

Methyl 2-(7,8-dibromohexadecyl)-acrylate: The dibromo acid product obtained in Example V, 2-(7,8-dibromohexadecyl)-acrylic acid, is dissolved in 50 ml of methanol and 5 ml of boron trifluoride methanol solution is added. The solution is heated under reflux for 6 hrs. The solution is concentrated to ½ volume and the acid is neutralized with saturated $NaHCO_3$ solution to about pH 7. The oily material is extracted with ether, washed with water and dried over $Na_2SO_4$. The ether solvent is removed under reduced pressure to give 4.80 g of crude oily product, methyl 2-(7,8-dibromohexadecyl)-acrylate.

EXAMPLE VIII

An equivalent quantity of each brominated acrylic acid obtained in Example VI is methylated according to the esterification procedure of Example VII to yield the following respective acrylates:
methyl 2-(2,3-dibromoundecyl)-acrylate;
methyl 2-(3,4-dibromododecyl)-acrylate;
methyl 2-(7,8-dibromotridecyl)-acrylate;
methyl 2-(2,3-dibromotetradecyl)-acrylate;
methyl 2-(7,8-dibromopentadecyl)-acrylate; and
methyl 2-(6,7-dibromohexadecyl)-acrylate.

EXAMPLE IX

Methyl 2-(7,8-dibromohexadecyl)-glycidate: A mixture of 3.80 g (0.0081 mole) of methyl 2-(7,8-dibromohexadecyl)-acrylate, 2.76 g (0.016 mole) of m-chloroperbenzoic acid and 50 mg of 3-t-butyl-4-hydroxy-5-methylphenyl sulfide in 50 ml of dry 1,2-dichloroethane is stirred and refluxed for 4 hrs. The mixture is cooled, filtered, and the filtrate concentrated, and about 100 ml of petroleum ether is added. The insoluble solid is filtered again and discarded. The filtrate is concentrated to dryness to give 4.2 g of oily residue. It is purified by dry column chromatography using 400 g of silica gel and eluting the column with 5% ether in petroleum ether. There is obtained 3.03 g of the pure oil, methyl 2-(7,8-dibromohexadecyl)-glycidate.

Anal. calcd. for $C_{20}H_{36}O_3Br_2$: C 49.60; H 7.49; Br 33.00%. Found: C 49.74; H 7.50; Br 33.24%.

EXAMPLE X

The procedure of Example IX is repeated using an equivalent amount of each methyl acrylate obtained in Example VIII as the starting material to yield the following respective glycidates:
methyl 2-(2,3-dibromoundecyl)-glycidate;
methyl 2-(3,4-dibromododecyl)-glycidate;
methyl 2-(7,8-dibromotridecyl)-glycidate;
methyl 2-(2,3-dibromotetradecyl)-glycidate;
methyl 2-(7,8-dibromopentadecyl)-glycidate; and
methyl 2-(6,7-dibromohexadecyl)-glycidate.

EXAMPLE XI

Methyl 2-(cis-7,8-hexadecenyl)-glycidate: To a stirred mixture of 3.32 g (0.0069 mole) of methyl 2-(7,8-dibromohexadecyl)-glycidate and 9.0 g of zinc dust in 150 ml of DMF is added 1.50 g of anhydrous potassium carbonate and a few crystals of iodine. The mixture is maintained at 50° C. for 3.5 hrs. The reaction is monitored by thin layer chromatography (TLC). The occasional addition of iodine crystals is employed to speed up the reaction. Ether is added and the zinc dust then removed by filtration. The filtrate is washed with water and dried over $Na_2SO_4$. On removal of the ether solvent there is obtained about 2.3 g of oily product which is purified by dry column chromatography using 100 g of silica gel and eluting it with 5% ether in petroleum ether. About 1.30 g of the pure oil, methyl 2-(cis-7,8-hexadecenyl)-glycidate is obtained.

Anal. calcd. for $C_{20}H_{36}O_3$: C 74.02; H 11.18%. Found: C 73.91; H 11.22%. NMR: ($CDCl_3$) 5.3 ppm (2H, olefinic); 3.73 ppm (3H, —$OCH_3$); 2.9 ppm (AB quartet, $J_{AB}$ = 8Hz).

EXAMPLE XII

An equivalent amount of each glycidate obtained in Example X is debrominated according to the procedure of Example XI to yield the following respective esters of formula (I):
methyl 2-(cis-2,3-undecenyl)-glycidate;
methyl 2-(cis-3,4-dodecenyl)-glycidate;
methyl 2-(cis-7,8-tridecenyl)-glycidate;
methyl 2-(cis-2,3-tetradecenyl)-glycidate;
methyl 2-(cis-7,8-pentadecenyl)-glycidate; and
methyl 2-(cis-6,7-hexadecenyl)-glycidate.

EXAMPLE XIII 2-(cis-7,8-Hexadecenyl)-glycidic acid: To 3.24 g (0.01 mole) of methyl 2-(cis-7,8-hexadecenyl)-glycidate at room temperature is added 10 ml methanol solution containing 0.857 g of anhydrous barium hydroxide. The mixture is stirred at room temperature for 48 hrs. The methanol is removed under reduced pressure and the oily residue is triturated with ether. The ether solution is decanted and the residue is triturated with ether again until solidification of the residue. The solid is collected on a filter, washed with ether and dried, giving about 2.90 g of the solid barium salt of 2-(7,8-dibromohexadecyl)-glycidic acid. The salt is placed in a flask and stirred with 10 ml of 1N HCl aqueous solution. Ether is added and the mixture is stirred for 20 min. The ether layer is separated, washed with water and dried. On removal of the ether solvent there is obtained 2-(cis-7,8-hexadecenyl)-glycidic acid.

EXAMPLE XIV

The ester-to-acid hydrolysis procedure of Example XIII is repeated with an equivalent quantity of each glycidate obtained in Example XII to yield the following respective acids of formula (I):
2-(cis-2,3-undecenyl)-glycidic acid;
2-(cis-3,4-dodecenyl)-glycidic acid;
2-(cis-7,8-tridecenyl)-glycidic acid;
2-(cis-2,3-tetradecenyl)-glycidic acid;
2-(cis-7,8-pentadecenyl)-glycidic acid; and
2-(cis-6,7-hexadecenyl)-glycidic acid.

EXAMPLE XV

Ethyl 2-(cis-7,8-hexadecenyl)-glycidate: 0.01 Mole of 2-(cis-7,8-hexadecenyl)-glycidic acid and an euqivalent stoichiometric amount of absolute ethanol in 600 ml of benzene containing 1 g of p-toluenesulfonic acid is heated under reflux with azeotropic removal of water for 7 hrs. The reaction mixture is filtered, washed with sodium bicarbonate solution, dried over anhydrous magnesium sulfate and the solvent evaporated in vacuo to give an oily residue of ethyl 2-(cis-7,8-hexadecenyl)-glycidate.

What is claimed is:

1. An alkenylglycidic acid derivative having the formula:

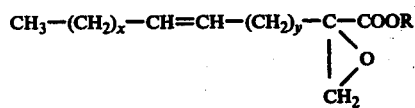

wherein x and y are each a positive integer the sum of which (x+y) equals an integer from 8 to 13, and R is a member selected from the group consisting of hydrogen and loweralkyl.

2. An alkenylglycidate of claim 1 wherein R is methyl.

3. Methyl 2-(cis-7,8-hexadecenyl)-glycidate.

4. 2-(cis-7,8-hexadecenyl)-glycidic acid.

* * * * *